United States Patent [19]

Allen et al.

[11] Patent Number: 4,670,406

[45] Date of Patent: Jun. 2, 1987

[54] TRACERS FOR USE IN ASSAYS

[75] Inventors: Stephen D. Allen, Park City, Utah; Michael Thompson, Evansville, Ind.

[73] Assignee: Becton Dickinson and Company, Franklin Lakes, N.J.

[21] Appl. No.: 568,482

[22] Filed: Jan. 6, 1984

[51] Int. Cl.$^4$ .................. G01N 33/53; G01N 33/549; G01N 33/533; G01N 33/534

[52] U.S. Cl. .................................. 436/500; 436/544; 436/545; 436/546; 436/532; 435/181

[58] Field of Search ............... 436/532, 500, 544–546, 436/800, 804, 817; 435/181

[56] References Cited

U.S. PATENT DOCUMENTS

| | | | |
|---|---|---|---|
| 4,007,089 | 2/1977 | Smith, III | 435/181 |
| 4,152,411 | 5/1979 | Schall, Jr. | 436/545 |
| 4,286,964 | 9/1981 | Seed | 436/532 |
| 4,419,444 | 12/1983 | Quash | 436/532 |
| 4,434,151 | 2/1984 | Byrne et al. | 424/1.1 |

FOREIGN PATENT DOCUMENTS 2609614  9/1977  Fed. Rep. of Germany ...... 436/532

*Primary Examiner*—Christine M. Nucker
*Attorney, Agent, or Firm*—Elliot M. Olstein

[57] ABSTRACT

Bifunctional aromatic compounds are employed as rigid coupling compounds for coupling one organic compound to another. For example, paranitrophenylisocyanate may be employed as a coupling compound for coupling thyroxine to a fluorescent dye to form a tracer for use in an assay.

28 Claims, No Drawings

TRACERS FOR USE IN ASSAYS

This invention relates to the coupling of one organic material to another, intermediates useful in producing coupled products, and uses for such coupled products.

Coupling agents or spacer compounds are generally bifunctional compounds which are employed for coupling one organic material to another. For example, in an assay, such as an immunoassay, one of the components of the assay is a tracer which is comprised of a ligand; for example, an antigen, coupled to a suitable marker; for example, a chromogen, such as a fluorescent dye. In producing such a tracer, in many cases, the antigen is coupled to the fluorescent dye by use of a bifunctional coupling agent or spacer.

Similarly, in an immunoassay employing a solid support, there is a need to couple a material used in the assay, such as an antibody, to a solid support, such as a polymer, and in some cases, this is accomplished by use of a coupling agent.

There is a need in the art for improved means of coupling one material to another through a coupling agent or spacer compound.

In accordance with one aspect of the present invention, there is provided intermediates for coupling one material to another.

In accordance with another aspect of the present invention, there is provided coupled compounds or materials.

In accordance with a further aspect of the invention, there is provided a process for preparing such coupling agents, intermediates and coupled compounds.

In accordance with yet another aspect of the invention, there is provided a process for using coupling agents, intermediates and coupled products.

More particularly, in accordance with one aspect of the present invention, there is provided an intermediate useful in preparing coupled compounds, which has the following structural formula:

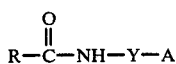
                                    I wherein
Y is a divalent aromatic hydrocarbon radical;
R is an organic radical having at least one active hydrogen substituent group (in particular, an amine, thiol or hydroxyl substituent group); and
A is selected from the group consisting of —NO₂; NH₂; —COOH;

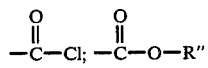

—N=C=O; —N=C=S; —SH; —OH; —COOR″;

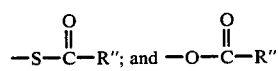

wherein R″ is alkyl.

In accordance with another aspect of the present invention, there is provided coupled compounds having the following structural formula:

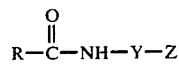
                                    II wherein
Z is selected from the group consisting of

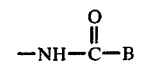

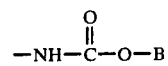

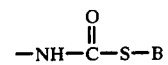

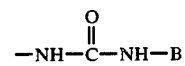

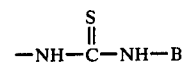

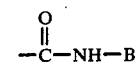

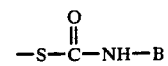

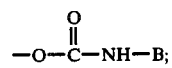

B is an organic radical;
R is an organic radical having at least one active hydrogen substituent group wherein R is coupled through the active substituent group (preferably an amine, thiol, or hydroxyl substituent group); and
Y is a divalent aromatic hydrocarbon radical.

In accordance with a particularly preferred embodiment of the invention, in the hereinabove described structural formulas, Y is a divalent benzene radical, although it is also to be understood that Y could be a divalent naphthalene or a divalent diphenyl radical.

The intermediates (I) may be prepared from compounds represented by structural formula (III):

                                    III

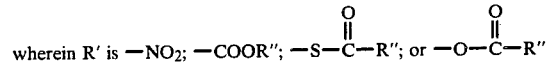

wherein
R and Y are hereinabove defined.
R' is generally in either the para-or meta- position, preferably para, with R' most preferably being —NO₂.

In the case where in Compound III, R' is NO , Compound III is initially coupled to an organic compound having an active hydrogen substituent group which is reactive with an isocyanate group to produce a Compound I wherein A is —NO . Subsequently, the —NO₂ group may be selectively reduced to an amino group (use of a reducing agent such as hydrogen and catalyst of sulfurated sodium borohydride) to provide a reactive group for coupling to another organic compound. Alternatively, the amino group may be converted to an isocyanate (reaction with phosgene) or isothiocyanate group (reaction with thiophosgene); either of which are reactive for coupling intermediate I to an organic compound.

In the case where, in Compound III, R' is —COOR",

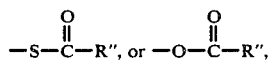

after coupling Compound III to an organic compound through the isocyanate substituent group, substituent group R' may be hydrolyzed to provide a substituent group A which is either —COOH, —SH or —OH, respectively, each of which is reactive for coupling intermediate I to an organic compound.

Thus, as should be apparent, Compound III is selected so as to include a substituent group R' which is not reactive with the active hydrogen substituent group of the organic compound to which Compound III is to be coupled through its isocyanate group. Subsequently, R' is converted to a substituent group A which is reactive with an active hydrogen substituent group of the organic compound to which intermediate I is to be coupled so as to produce coupled compound II.

The compound represented by structural formula I may be employed for producing coupled compounds, as represented by structural formula II. In using the compound represented by structural formula I, the substituent group represented by A is one which is capable of reacting with an active hydrogen substituent group on the compound to which the compound represented by structural formula I is to be coupled. Thus, for example, when A is an amino group, compound I may be coupled to an organic compound having a carboxyl substituent group by procedures generally known in the art. Similarly, when A is carboxyl, compound I may be coupled to an organic compound which has either an amino substituent group or an isocyanate substituent group by procedures known in the art. When A is isocyanate, compound I may be coupled to an organic compound which has an active hydrogen substituent group which is either mercapto (thiol), hydroxy, carboxyl or amino. When A is thiol or hydroxy, compound I may be coupled to an organic compound which has an active hydrogen substituent group which is isocyanate. When A is isothiocyanate, compound I may be coupled to an organic compound which has an amino substituent group. The procedures for accomplishing such coupling through such functional groups are generally known in the art.

The coupling agents III may be employed for coupling a wide variety of organic materials to each other. Thus, for example, the coupling compounds III may be employed for producing tracers which are to be used in an assay wherein such tracer is comprised of a detectable marker; e.g., a radioactive marker, chromogen, enzyme, etc., coupled to a ligand (the term "ligand" as used herein refers to a hapten, antigen or antibody). In such an embodiment, one of the marker or ligand includes a substituent group which is capable of reacting with an isocyanate group, and the substituent group R' of coupling agent III is non-reactive with the substituent group on the ligand or marker. After the coupling agent III is coupled to the ligand or marker, there is produced an intermediate compound I wherein the substituent group A is nonreactive with the active hydrogen substituent group which is on the ligand or marker which has been initially coupled to produce intermediate I. The intermediate compound I is then coupled to the other of the marker or ligand, and if the substituent group A of intermediate I is not reactive with the active hydrogen substituent group on the other of the ligand or marker, then the substituent group A is selectively converted to a substituent group, as defined, which is reactive with the active hydrogen substituent group on the other of the ligand or marker. The intermediate I is then coupled to the other of the ligand or marker to produce a coupled compound II.

Thus, in producing a tracer for use in an assay, in coupled compounds II, one of R and B is a marker, such as a chromogen, an organic compound including a radioactive substituent group or an enzyme, and the other of R and B is a ligand. Thus, for example, in producing a fluorescent tracer, one of R and B is derived from a fluorescent dye having a substituent group which can be coupled to either isocyanate, or one of the reactive functional groups represented by A in structural formula I, and the other of R and B is derived from a ligand having a substituent group which can be coupled to the other of the isocyanate or reactive substituent group represented by A in structural formula I. In producing such a tracer, either the ligand or the fluorescent dye can be initially coupled to the isocyanate functional group of coupling agent III.

Applicant has found that the use of a coupling agent represented by structural formula III is particularly advantageous for producing fluorescent tracers, in that the coupling agent is rigid, whereby the fluorescent marker does not "fold" back onto the ligand, thereby minimizing the possibility of quenching of the fluorescent compound by the ligand.

As representative examples of suitable chromogens, there may be mentioned: acridine dyes, azure dyes, quinone dyes, Nile blue, Cresyl Violet, fluoresceins, rhodamines, coumarines, amino naphthalene derivatives (dansyl compounds), carbocyanines, indoles, lanthanide chelates, etc.

Thus, for example, a $T_4$ tracer may be prepared by initially coupling p-nitrophenylisocyanate to the amino moiety of thyroxine ($T_4$) wherein the carboxyl and hydroxyl moieties of the $T_4$ is appropriately blocked. The nitro group is reduced to amine (Compound I, R is blocked $T_4$ radical, Y is benzene and A is amine), and the amino portion of Compound I may be coupled to a fluorescent dye including, for example, an isothiocyanate group; in particular fluorescein isothiocyanate. Alternatively, the amino group of Compound I may be converted to isothiocyanate by reaction with thiophosgene (in Compound I A is isothiocyanate), followed by reaction of Compound I with a fluorescent dye including an amino group; in particular fluorescein amine.

Similarly, a digoxin tracer may be produced by coupling digoxin to p-nitrophenylisocyanate, followed by reduction of nitro to amine, and reaction with a fluorescent dye, such as fluorescein isothiocyanate.

Although the present invention has particular use for producing fluorescent tracers, as hereinabove noted, the present invention may also be employed for producing other tracers, such as radioactive tracers, enzyme tracers, etc. As representative examples of suitable radioactive markers for producing radioactive tracers, there may be mentioned: hydroxyphenyl substituted amines or amino acids, wherein the phenyl group includes one or more radioactive substituent groups, such as radioiodinated tyrosine or tyramine; imidazole substituted amino acids or amines wherein the imidazole group is substituted with one or more radioactive substituent groups, and the like.

As representative examples of suitable enzyme markers, there may be mentioned: peroxidases, β-galacosidase, acetylcholine esterase, glucoamilase, maleic acid dehydrogenase, glucose-6-phosphoric acid dehydrogenase, glutaroxidase, acid phosphatase, etc.

As known in the art, the solid support may be a polymer, provided that the polymer includes a substituent group capable of reacting with either the isocyanate functionality or one of the reactive substituents represented by A of intermediate I; e.g., polyacrylamide, poly (aminostyrene), etc.

The tracers and supported ligands prepared in accordance with the present invention may be employed in an assay for a wide variety of analytes (the term "analytes" refers to a hapten, antigen or antibody), of a type generally known in the art. Thus, for example, the present invention is applicable to assays for drugs, including therapeutic drugs and so-called "drugs of abuse"; steroids, vitamins, sugars, amino acids, polypeptides, proteins, various hormones, antibiotics, viruses, etc.

The tracers and supported ligands prepared in accordance with the present invention may be employed in an immunoassay (the term "immunoassay" is used in a generic sense and includes assays which use naturally occurring binders instead of an antigen or antibody, and which are sometimes referred to as competitive protein binding assays), and as known in the art, one of the components of the assay is a binder. In the case where the analyte is a hapten or antigen, the binder may be an antibody or naturally occurring substance which has one or more binding sites specific for the analyte, and in a case where the analyte is an antibody, the binder may be an antigen to the antibody or an antibody elicited in response to the analyte. The selection of a suitable binder is deemed to be within the scope of those skilled in the art, and no further details in this respect are deemed necessary for a complete understanding of the invention.

In the assay, the ligand portion of the tracer used in the assay is determined by the type of assay to be employed. Thus, for example, if the assay is for an analyte which is either an antigen or hapten, the ligand portion of the tracer is either the antigen or hapten to be assayed or appropriate analog thereof (the term "appropriate analog" means an analog of the analyte which is bound by the binder used in the assay). Alternatively, the ligand portion of the tracer may be a binder for the hapten or antigen to be assayed, in which case the assay is designed so that the analyte inhibits binding of the tracer to binding sites specific for the tracer.

In the case where the analyte is an antibody, the ligand portion of the tracer may be the antibody or appropriate analog thereof, in which case both the antibody and the tracer would compete for a limited number of binding sites specific for both the antibody analyte and the tracer. Alternatively, the ligand portion of the tracer may be an antigen to the antibody analyte or antibody elicited in response to the antibody analyte, in which case, the antibody analyte inhibits binding of the tracer to binding sites specific for the tracer.

In some cases, where the analyte is to be determined by a so-called "sandwich type" of assay, the ligand portion of the tracer has binding sites specific to the analyte, which analyte has multiple determinant sites.

The selection of a suitable ligand for use as the ligand portion of the tracer is deemed to be within the scope of those skilled in the art from the teachings herein and, accordingly, no further details in this respect are deemed necessary for a complete understanding of the present invention.

The coupling agents of the present invention may also be employed for coupling a therapeutic agent to an antibody, and in particular a monoclonal antibody. In such a case, in coupled compound II, R is derived from a therapeutic agent, and B is derived from an antibody.

Thus, as should be apparent from the hereinabove description, the coupled compound II may be produced from a wide variety of organic compounds, with the organic radical represented by R in compound II being derived from one organic compound, and the organic radical represented by B in coupled compound II being derived from another organic compound, provided that the respective organic compounds include appropriate active hydrogen substituent groups for reacting with the appropriate substituent group in coupling agent III (isocyanate) or the appropriate reactive substituent group represented by A in structural formula I. Thus, in the coupled compound II, R may be an organic radical derived from organic compounds which include an active hydrogen group capable of reacting with an isocyanate group, which organic compound may be a marker (radioactive substituted organic compound, a chromogen, preferably a fluorescent dye, an enzyme), or a ligand, and in particular, a nonprotein antigen or a nonprotein hapten, a solid support or a therapeutic agent (in particular, a drug). Similarly, B may be an organic radical derived from an organic compound which includes an active hydrogen substituent group capable of reacting with one of the reactive substituent groups represented by A in intermediate I. Thus, B may be an organic radical derived from an organic compound which may be a protein, antibody, a hapten, an antigen, a chromogen (a dye, preferably a fluorescent dye), an enzyme, an organic compound having a radioactive substituent group, a polymer, etc.

The present invention will be further described with respect to the following examples; however, the scope of the invention is not to be limited thereby:

EXAMPLE 1

2.1 millimoles of trimethylsilylchloride (TMS-Cl) is added to 1 millimole of Thyroxine ($T_4$) in anhydrous pyridine under nitrogen. After the reaction, 1.1 moles of p-nitrophenylisocyanate in anhydrous pyridine is added to the reaction mixture and the mixture is stirred for about 48 hours under nitrogen. The reaction is monitored by TLC. After 48 hours, the mixture is diluted with methanol and the volatiles are removed. The crude reaction mixture is purified by Prep TLC or high performance liquid chromatography (HPLC) or by other chromatography. The resulting product is paranitrophenylisocyanato -$T_4$.

The above reactions are accomplished at room temperature and pressure (STP).

The nitro group is reduced to amine by addition of 0.55 millimoles (excess over the concentration of initial $T_4$ used) of sulfurated sodium borohydride to 0.5 millimoles of the above product in ether, at room temperature and pressure. The reaction is accomplished by mixing for about 3 to 4 hours, and monitoring conversion of nitro to amine by IR. The resulting product is para-aminophenyl isocyanato-$T_4$.

To the above product, there is added a molar equivalent of isothiocyanato-fluorescein, followed by stirring for about 48 to 72 hours. The product is purified by chromatography.

The resulting product is a fluorescent tracer wherein fluorescein isothiocyanate is coupled to $T_4$ through a rigid coupling agent, and such tracer may be employed in an assay for $T_4$.

EXAMPLE 2

Preparation of Digoxin Fluorescent Tracer

A solution of 1.1 millimoles of para-nitrophenyl isocyanate in dry pyridine is added to a solution of 1 millimole of digoxin in dry pyridine under nitrogen. After 2 hours, the pyridine is removed and the crude product is purified by chromatography.

The desired product is Compound I wherein Y is a benzene radical, A is $NO_2$, and R is a 15'-digoxin radical.

This product is then treated with one equivalent of sulfurated sodium borohydride ($NaBH_2S_3$). A solution of 1 equivalent of the above product in anhydrous tetrahydrofuran is added to a solution of 1 equivalent of sulfurated sodium borohydride in anhydrous tetrahydrofuran at room temperature under nitrogen. Product formation can be followed by IR (conversion of $NO_2-NH_2$).

This product is isolated and purified by chromatography.

The above product is dissolved in pyridine and added to a solution of 1 equivalent of Fluorescein isothiocyanate in pyridine at room temperature under nitrogen. After 72 hours, the new product, a fluorescent digoxin species, is purified by chromatography.

The resulting product is a compound II wherein R is a 15' digoxin radical; Z is

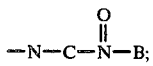

B is a fluorescein radical; and Y is a divalent benzene radical.

To a mixture of 100 millimoles of 15'-p-amino-phenyl carbamoyl digoxin (as prepared in Example 2) in dry pyridine under nitrogen, 100 millimoles of thiophosgene is added over 3-4 minutes. After 4 hours, the solvent is removed under reduced pressure. The resulting product can be purified by chromotography.

The resulting product is Compound I wherein Y is a divalent benzene radical; R is 15' digoxin radical' and A is $-N=C=S$.

Once isolated and purified, this compound would be stable over several months before requiring any further purification. The product should be kept dessicated in the freezer.

EXAMPLE 4

Reaction of 15' p-isothiocyanatophenylcarbamoyl-digoxin with an enzyme (acid phosphatase).

A mixture of excess (20 to 50 fold) of isothiocyanate in a minimum amount of dimethylsulfoxide is added to a mixture of an appropriate enzyme in phosphate, carbanate or borate buffer at pH 9.5 and 10 mM at 4° C. After 24 hours, the mixture is dialyzed to get rid of dimethylsulfoxide and excess digoxin intermediate. For further purification, chromatography is employed.

This product is Compound II wherein R is a digoxin radical; Y is a divalent benzene radical; Z is NH—C—NH—B and B is an acid phosphatase enzyme radical.

The above procedures are illustrative and may be similarly employed for coupling a wide variety of organic compounds to each other, provided that the organic compounds have the required active hydrogen substituted groups. Thus, the above procedures are applicable to the coupling of ligands other than digoxin or $T_4$ to organic compounds other than fluorescein dyes and/or enzymes.

The present invention is particularly advantageous, in that, by use of Compound III it is possible to produce coupled products II in which there is a rigid coupling of one organic compound to another. This is of advantage when producing fluorescent tracers in that the rigidity of the coupling reduces quenching of the fluorescent compound by the ligand. Thus, for example, the heavy atom effect on a fluorescent material (for example, the iodine groups of $T_3$ and/or $T_4$), which can quench a fluorescent material is reduced and/or eliminated. Thus, the invention has particular use in the production of a thyroid hormone tracer wherein a thyroid hormone ($T_3$ or $T_4$) is coupled to a fluorescent compound.

Numerous modifications and variations of the present invention are possible in light of the above teachings and, therefore, within the scope of the appended claims the invention may be practiced otherwise than as particularly described.

What is claimed is:
1. A composition of matter comprising:
a compound having structural formula I:

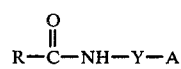

wherein
Y is a divalent aromatic hydrocarbon radical;
R is an organic radical having at least one active hydrogen substituent group wherein R is a detectable marker or a ligand selected from the group consisting of haptens and antigens coupled through the active hydrogen substituent group; and
A is selected from the group consisting of $-NO_2$; $-NH_2$; $-COOH$;

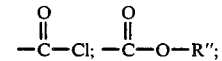

$-N=C=S$; $-SH$; $-OH$; $-N=C=O$;

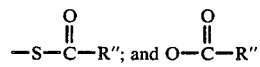

wherein R″ is alkyl.

2. The composition of claim 1 wherein Y is a divalent benzene radical.
3. The composition of claim 2 wherein A is $-NO_2$.
4. The composition of claim 2 wherein A is $-NH_2$.
5. The composition of claim 2 wherein A is $-N=C=S$.
6. The composition of claim 2 wherein A is $-N=C=O$.
7. The composition of claim 2 wherein R is a digoxin radical.

8. The composition of claim 2 wherein R is a thyroxine radical.

9. The composition of claim 2 wherein R is detectable marker.

10. A composition of matter comprising a (compound) tracer having structural formula II:

$$R-\overset{O}{\underset{\|}{C}}-NH-Y-Z \qquad II$$

wherein
Z is selected from the group consisting of $$-NH-\overset{O}{\underset{\|}{C}}-B$$

$$-NH-\overset{O}{\underset{\|}{C}}-O-B$$

$$-NH-\overset{O}{\underset{\|}{C}}-S-B$$

$$-NH-\overset{O}{\underset{\|}{C}}-NH-B$$

$$-NH-\overset{S}{\underset{\|}{C}}-NH-B$$

$$-\overset{O}{\underset{\|}{C}}-NH-B$$

$$-S-\overset{O}{\underset{\|}{C}}-NH-B$$

$$-O-\overset{O}{\underset{\|}{C}}-NH-B;$$

B is an organic radical;
R is an organic radical having at least one active hydrogen substituent group wherein R is coupled through the active substituent group wherein one of R and B is a detectable marker and the other of R and B is a ligand selected from the group consisting of antigens, haptens and antibodies; and
Y is a divalent aromatic hydrocarbon radical.

11. The composition of claim 10 wherein Y is a divalent benzene radical.

12. The composition of claim 11 wherein R is a ligand selected from the group consisting of haptens and antigens.

13. The composition of claim 12 wherein B is a detectable marker.

14. The composition of claim 13 wherein the marker is a fluorescent dye.

15. The composition of claim 14 wherein the marker is a fluorescein dye.

16. The composition of claim 13 wherein R is a digoxin radical.

17. The composition of claim 16 wherein B is a fluorescent dye.

18. The composition of claim 17 wherein B is a fluorescein dye.

19. The composition of claim 13 wherein R is a thyroxine radical.

20. The composition of claim 19 wherein B is a fluorescent dye.

21. The composition of claim 20 wherein B is a fluorescein dye.

22. In an assay for an analyte which uses a tracer and a binder to produce both bound and unbound tracer, the improvement comprising:
employing as a tracer the composition of claim 19; and determining at least one of bound and unbound tracer as a measure of analyte.

23. In an assay for an analyte which uses a tracer and a binder to produce both bound and unbound tracer, the improvement comprising:
employing as a tracer the composition of claim 13; and determining at least one of bound and unbound tracer as a measure of analyte.

24. In an assay for an analyte which uses a tracer and a binder to produce both bound and unbound tracer, the improving comprising:
employing as a tracer the composition of claim 14; and determining at least one of bound and unbound tracer as a measure of analyte.

25. In an assay for an analyte which uses a tracer and a binder to produce both bound and unbound tracer, the improvement comprising:
employing as a tracer the composition of claim 16; and determining at least one of bound and unbound tracer as a measure of analyte.

26. In an assay for an analyte which uses a tracer and a binder to produce both bound and unbound tracer, the improvement comprising:
employing as a tracer the composition of claim 19; and determining at least one of bound and unbound tracer as a measure of analyte.

27. The composition of claim 14 wherein R is a thyroid hormone radical.

28. In an assay for a thyroid hormone which uses a tracer and a binder to produce both bound and unboudn tracer, the improvement comprising:
employing as a tracer the composition of claim 27; and determining at least one of bound and unbound tracer as a measure of analyte.

* * * * *